(12) United States Patent
Fedyk et al.

(10) Patent No.: US 8,303,558 B2
(45) Date of Patent: Nov. 6, 2012

(54) TAMPON APPLICATOR HAVING CORRUGATED GRIP

(75) Inventors: Glen Charles Fedyk, Fairfield Township, OH (US); Nancy Karapasha, Cincinnati, OH (US); Charles John Berg, Jr., Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1492 days.

(21) Appl. No.: 10/179,136

(22) Filed: Jun. 25, 2002

(65) Prior Publication Data

US 2003/0236485 A1    Dec. 25, 2003

(51) Int. Cl.
*A61F 13/20*    (2006.01)

(52) U.S. Cl. ............... 604/385.17; 604/385.18; 604/11; 604/18

(58) Field of Classification Search ............ 604/11–18, 604/57, 59, 60, 385.17, 385.18
See application file for complete search history.

(56) References Cited

U.S. PATENT DOCUMENTS

| | | | | |
|---|---|---|---|---|
| 3,575,169 | A | * | 4/1971 | Voss et al. ............... 604/18 |
| D250,049 | S | * | 10/1978 | Hite, Jr. ............... D24/141 |
| D279,504 | S | * | 7/1985 | Tump ............... D24/114 |
| 4,573,963 | A | * | 3/1986 | Sheldon |
| 4,822,332 | A | * | 4/1989 | Kajander |
| 5,330,421 | A | | 7/1994 | Tarr et al. |
| 5,607,415 | A | | 3/1997 | Datta et al. |
| 5,665,186 | A | | 9/1997 | Datta et al. |
| 5,709,652 | A | | 1/1998 | Hagerty |
| 5,823,988 | A | * | 10/1998 | Orenga et al. |
| 6,171,682 | B1 | | 1/2001 | Raidel et al. |
| 6,264,626 | B1 | | 7/2001 | Linares et al. |
| 6,368,442 | B1 | * | 4/2002 | Linares et al. |
| 6,416,488 | B1 | * | 7/2002 | Jackson et al. ............... 604/15 |

FOREIGN PATENT DOCUMENTS

| | | |
|---|---|---|
| DE | 27 55 012 | 6/1978 |
| EP | 0 918 501 B1 | 8/2001 |
| GB | 2 166 656 | 5/1986 |
| JP | 53-074795 | 7/1978 |
| JP | H04-24412 | 2/1992 |

OTHER PUBLICATIONS

PCT International Search Report dated May 11, 2003.
Japanese Office Action mailed Oct. 28, 2008 from Suzuye & Suzuye.

* cited by examiner

*Primary Examiner* — Jacqueline F. Stephens
(74) *Attorney, Agent, or Firm* — James B. Oehlenschlager; Megan C. Hymore

(57) ABSTRACT

A tampon applicator which has an elongate insertion member having a length extending from an insertion end to a gripper end opposite. The gripper end has a grip region dimensioned to substantially accept a user's grip. The grip region has a plurality of corrugations, a first transition portion, and a second transition portion. Each corrugation has a trough and a ridge. The first transition portion is substantially adjacent the gripper end and a second transition portion is disposed toward the insertion end.

8 Claims, 5 Drawing Sheets

TAMPON APPLICATOR HAVING CORRUGATED GRIP

FIELD OF THE INVENTION

This invention relates to a tampon applicator having a grip region for facilitating the insertion of a tampon into a body cavity.

BACKGROUND OF THE INVENTION

Applicators for delivering materials into a body cavity typically comprise a tubular insertion member having an insertion end and a gripper end opposite thereof, and an elongate expulsion member slidably fitted within the tubular insertion member for expelling the contained materials. The gripper end will generally incorporate features to allow a user to more or less securely hold the applicator during use, which includes the following steps: inserting the applicator into a body cavity, expelling a substantially enclosed material contained by the applicator, and withdrawing the applicator from the body.

Over the years, attempts have been made to improve the gripping features. One approach is to significantly reduce the diameter of the applicator in the gripper end. While a reduced diameter grip may help in preventing fingers from slipping during insertion, there is little or no resistance offered in the opposite direction of the insertion direction during the expulsion step. This is a step with which many users have difficulty.

Another approach to improve the grip of the applicator during use is to incorporate projections, such as in the form of a ring, at the base of the applicator member being inserted into the body. Similar to the disadvantage of applicators employing a reduced diameter in the gripping end, projections typically provide only a single direction of resistance.

While many have tried to design and manufacture tampon applicators having these improved qualities, there still remains a need for a tampon applicator that has gripping features that provide limited resistance to finger slip during the insertion and the expulsion of the tampon applicator.

SUMMARY OF THE INVENTION

The present invention encompasses a tampon applicator comprising an elongate insertion member having a length extending from an insertion end to a gripper end opposite thereof. The gripper end comprises a grip region dimensioned to substantially accept a user's grip. The grip region has a plurality of corrugations, a first transition portion, and a second transition portion. Each corrugation has a trough and a ridge. The first transition portion is substantially adjacent the gripper end and the second transition portion is disposed toward the insertion end. In one embodiment, the first transition portion and grip region span a radial arc identified as angle alpha ($\alpha$). In another embodiment, the second transition portion and grip region span a radial arc identified as angle beta ( ).

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

Figure 1:
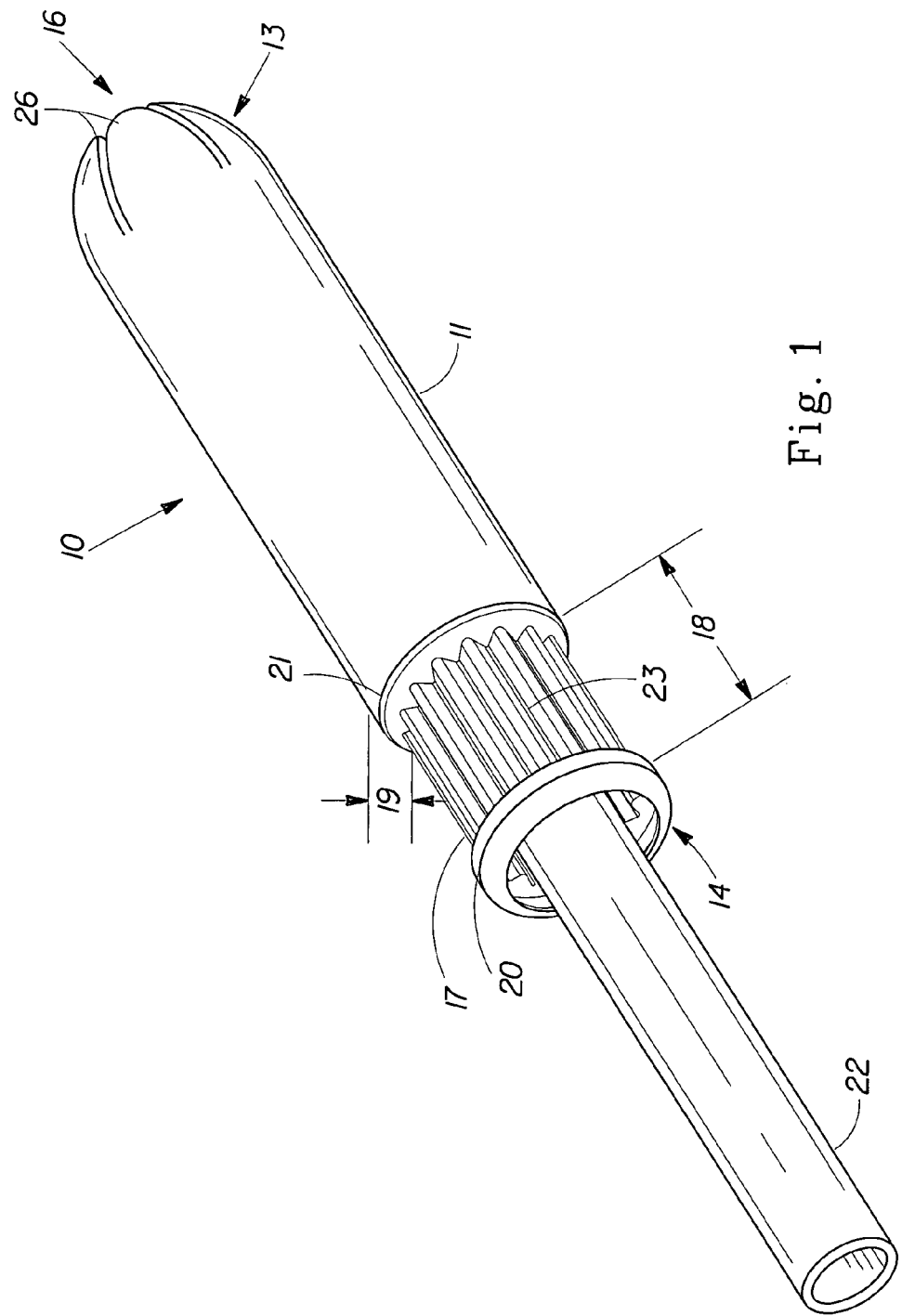
FIG. 1 is a perspective view of a tampon applicator comprising a grip region having a plurality of corrugations.

All documents cited are, in relevant part, incorporated herein by reference; the citation of any document is not to be construed as an admission that it is prior art with respect to the present invention.

Section I. will provide terms which will assist the reader in best understanding the features of the invention and not to introduce limitations in the terms inconsistent with the context in which they are used in this specification. These definitions are not intended to be limiting. Section II. will discuss the tampon applicator that results from the method of making the tampon applicator. Section III. will discuss a useful method in making a corrugated tampon grip.

I. Terms

In general in this specification, the term "tampon" is used to refer to a finished tampon after the compression process referred to below. As used herein the term "tampon" refers to any type of absorbent structure that is inserted into the vaginal canal or other body cavities for the absorption of fluid therefrom. Typically, tampons are constructed from an absorbent material that has been compressed in one or more steps employing one or more parts of the absorbent material in the radial direction, axially along the longitudinal and lateral axes or in both the radial and axial directions to provide a tampon, which is of a size and stability to allow insertion within the vagina or other body cavity. A tampon that has been so compressed is referred to herein as a "self-sustaining" form. The term "self-sustaining" is defined below. The tampon can be made from natural or synthetic fibers including cellulose fibers such as cotton or rayon, or artificial fibers such as polyester, polypropylene, nylon or blends thereof. Other types of fibers may also be used, such as cellulose sponge or a sponge formed from elastomeric materials.

As used herein, "self-sustaining" is a measure of the degree or sufficiency to which the tampon retains the compression applied to the absorbent material of the tampon pledget such that in the subsequent absence of the external forces, the resulting tampon will tend to retain its general shape and size. It will be understood by one of skill in the art that this self-sustaining form need not, and preferably does not persist during actual use of the tampon. That is, once the tampon is inserted and begins to acquire fluid, the tampon will begin to expand and may lose its self-sustaining form.

As used herein the terms "vaginal cavity," "within the vagina," and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina) and the cervix and is not intended to include the interlabial space, including the floor of vestibule. The externally visible genitalia generally is not included within the term "vaginal cavity" as used herein. As used herein, "vaginally insertable shape" refers to the geometrical form of the absorbent tampon after compression. While not to be limited to such dimensions, a typical compressed tampon for human use is 10-16 millimeters wide and 30-60 millimeters long depending on absorbency. For other mammals, typical tampon dimensions may vary based on differences in vaginal cavity geometry. While the tampon may be compressed into a substantially cylindrical configuration, other shapes are possible. These may include shapes having a cross section or cross-section element that may be described as rectangular, triangular, trapezoidal, semi-circular, hourglass, or other suitable shapes.

Figure 2:
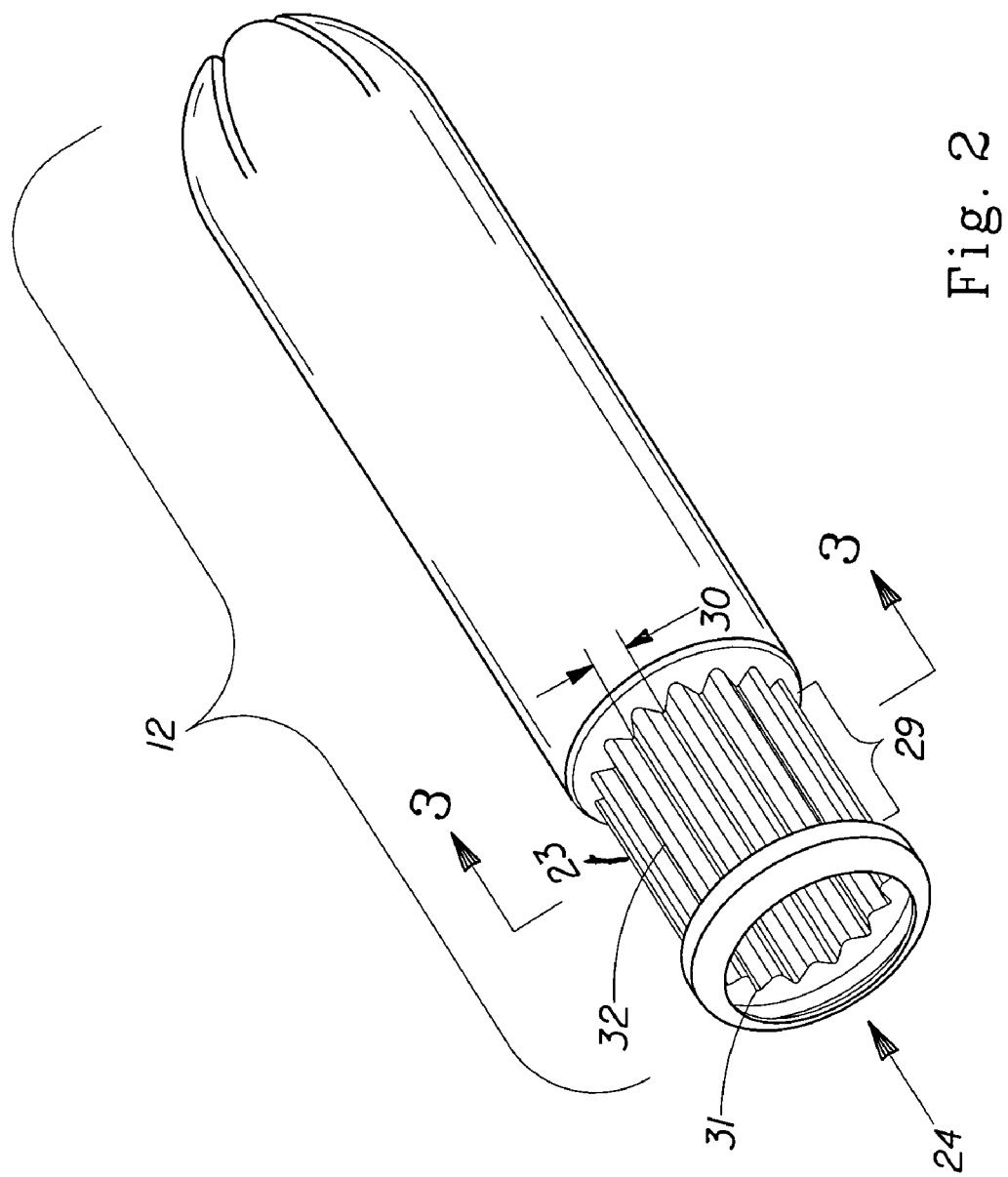
FIG. 2 is a perspective view of the elongate insertion member.

The "X axis" of a tampon is the axis which runs longitudinally through the center of the tampon insertion member 11 as shown in FIG. 2.

The "perimeter" of a segment of the tampon applicator is a distance measured around the outer surface of the tampon applicator perpendicular to the X axis. The perimeter may be measured by any common or known means.

II. Tampon Applicator of the Present Invention

Referring to FIGS. 1-2, a tampon applicator 10 is shown which is designed to house a tampon and provide a comfortable means of inserting the tampon into a woman's vagina.

The present invention relates to tampon applicators for delivering materials into body cavities, comprising elongate insertion members 11 that are intended to be at least partially inserted into a body cavity. The elongate insertion members 11 have an insertion end 13 and gripper end 14 opposite thereof. To improve a user's ability to securely hold the applicator during use, the gripper end 14 of the insertion member 11 employs a grip region 17 with at least one corrugation 23. The grip region 17 functions to provide a means for the user to grip the elongate insertion member 11 and hold it between her thumb and middle finger. The user can then position her forefinger on the free end of the elongate expulsion member 22 and orient the elongate insertion member 11 relative to her vagina while she pushes the elongate expulsion member 22 which is slidably mounted in the insertion member 11 into the elongate insertion member 11. The grip region 17 provides a means for orienting the applicator to positively guide its insertion.

The elongate expulsion member 22 functions by telescopically moving relative to the elongate insertion member 11. As the elongate expulsion member 22 is pushed into the elongate insertion member 11, the tampon is forced forward toward the insertion end 13 to radially open to a diameter which is sufficient to allow the tampon to be expelled from the elongate insertion member 11. With the tampon properly positioned in the woman's vagina, the tampon applicator 10 is withdrawn and properly discarded.

Figure 3:
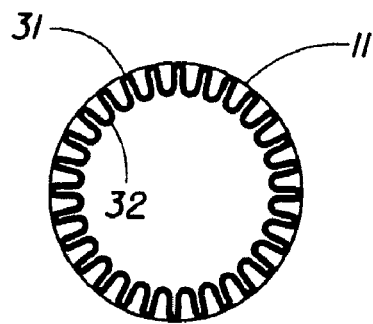
FIG. 3 is a cross-section along lines 3-3 of FIG. 2.

Referring to FIGS. 1-3, FIG. 1 depicts an applicator 10, comprising a tubular insertion member 11, having a length 12 (shown in FIG. 2) that runs from an insertion end 13 to a gripper end 14.

The insertion end 13 located on the insertion member 11 may be open-ended or comprise a partially or more fully closed-end which is often intended to be opened as the tampon is forced against it. The closed-end can be comprised of similar materials integral with or different from those of the insertion member 11. The closed-end designs and forms can comprise other designs or means such as but not limited to corrugations, petals, thin frangible caps such as film or paper caps, etc. The insertion end 11 can use plastic, paper, foil, polymer and fiber compositions for materials.

Figure 4:
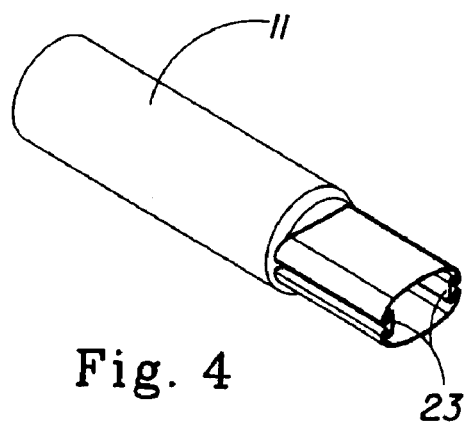
FIG. 4 is a perspective view of an alternative embodiment of a tampon applicator having a grip region with two corrugations.
Figure 7:
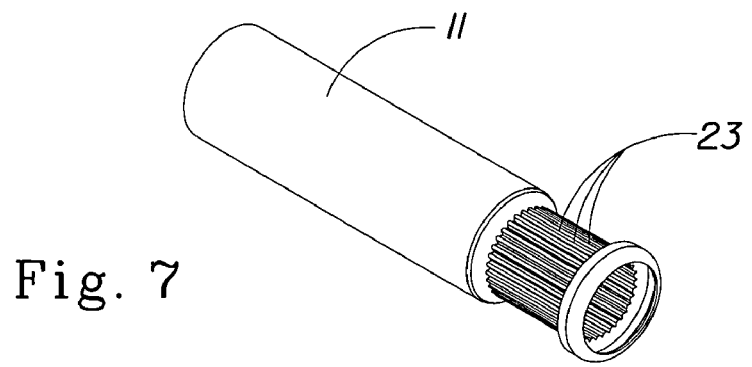
FIG. 7 is a perspective view of an alternative embodiment of the gripper region.
Figure 8:
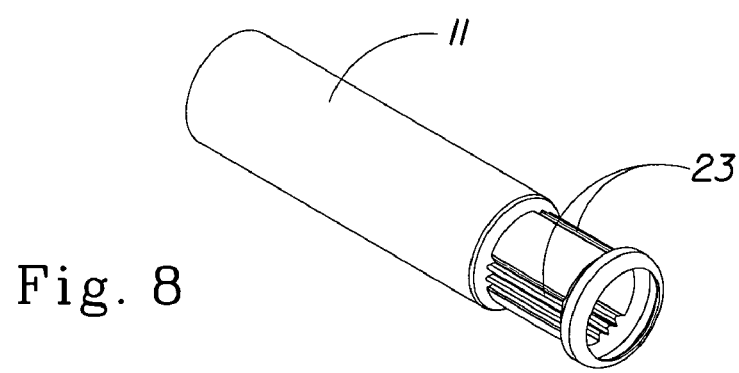
FIG. 8 is a perspective view of an alternative embodiment of the gripper region.
Figure 9:
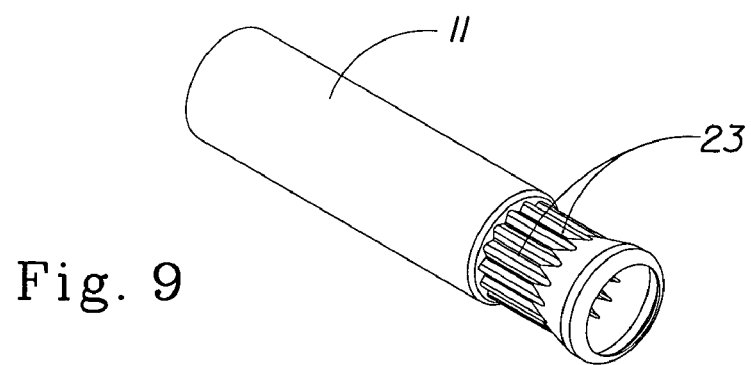
FIG. 9 is a perspective view of an alternative embodiment of the gripper region.

Referring primarily to FIG. 1, the gripper end 14 comprises a grip region 17 having a perimeter 24 (shown in FIG. 2) and a length 18. The grip region 17 has a first transition portion 20 and the second transition portion 21. The first transition portion 20 and a second transition portion 21 are located on either end of the grip region 17. The grip region 17 also has at least one corrugation 23. In an alternative embodiment, FIG. 4 shows an insertion member 11 with two corrugations 23. As seen in FIGS. 7, 8, and 9, the corrugations 23 may cover from a small area of the grip region 17 to the entire area of the grip region 17.

Referring to FIG. 2, the perimeter 24 of the grip region 17 may take essentially any desired shape, including ovals, circles, and various other geometric patters. As shown in FIG. 1 and FIG. 2 the grip region is substantially circular shaped. In an alternative embodiment shown in FIG. 4, an elongate insertion member 11 has an elliptical shaped grip region 17.

Referring to FIG. 1, it is important for the length 18 of the grip region 17 to be of sufficient dimension to substantially accept a user's grip within the confines of both the first transition portion 20 and the second transition portion 21. The length 18 and depth 19 of the grip region 17 both provide for secure handling of the tubular insertion member 11. If a user's grip does not substantially fit within the grip region 17, then excess bridging of one or more of the transition portions may occur, substantially compromising the benefits provided by the grip region 17 and transition portions, as described in detail below. As used in the specification and claims, the term "user's grip" means any way of holding the tampon applicator from a hand, e.g. a thumb or finger. The length 18 of the grip region 17 is from about 10 millimeters to about 20 millimeters.

Figure 5:
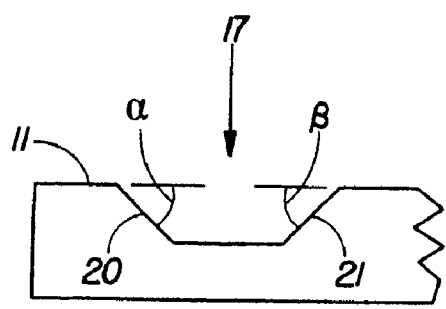
FIG. 5 is a cross-section along lines 3-3 of FIG. 2 of an alternative embodiment of the gripper region.
Figure 6:
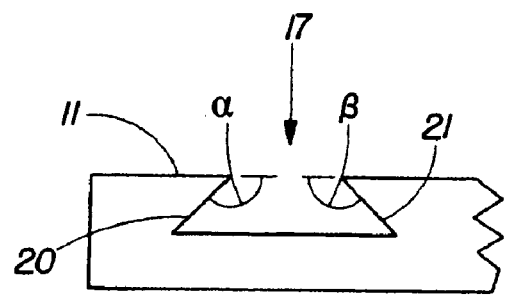
FIG. 6 is a cross-section along lines 3-3 of FIG. 2 of an alternative embodiment of the gripper region.
Figure 10:
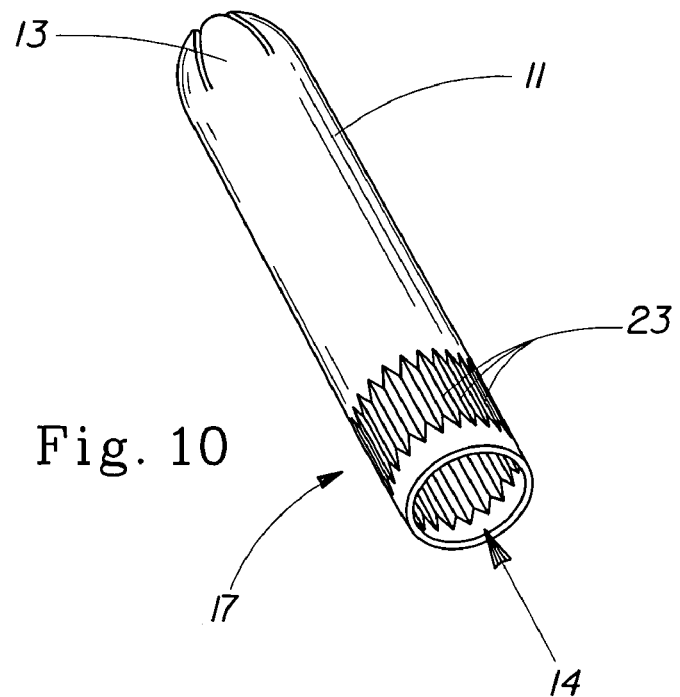
FIG. 10 is a perspective view of an alternative embodiment of the gripper region.
Figure 11:
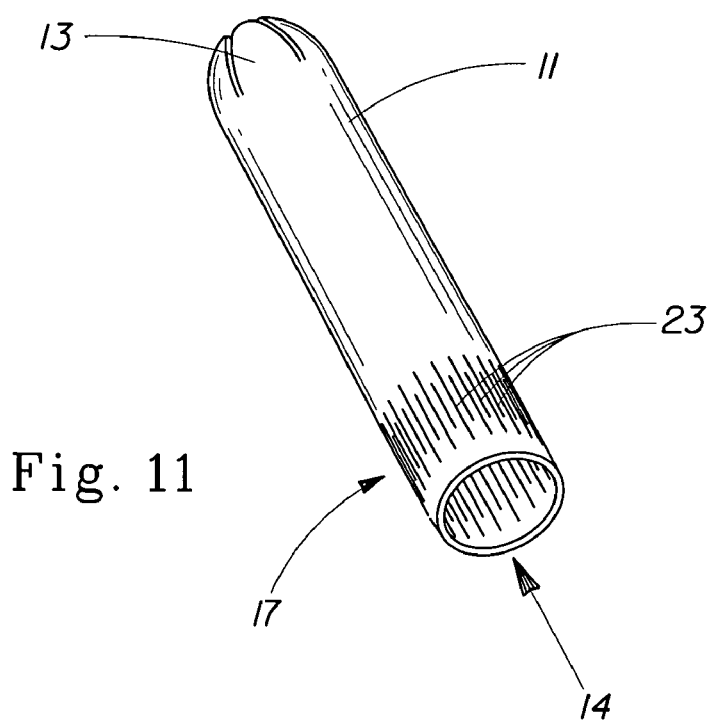
FIG. 11 is a perspective view of an alternative embodiment of the gripper region.

In FIG. 1, the first transition portion 20 and the grip region 17 span a radial arc, identified as angle alpha ($\alpha$), which extends from the first transition portion 20 to the grip region 17. The angle alpha ($\alpha$) can be between about 0° to about 180°. In FIG. 1, the second transition portion 21 and the grip region 17 span a radial arc, identified as an angle beta (, which extends from the second transition portion 21 to the grip region 17. The angle beta ($\beta$) can be between about 0° to about 180°. For example, the alpha angle can be 90° and the beta angle can be greater than 90°. An alternative embodiment is shown in FIG. 5 where the alpha angle and the beta angle are less than 90°. Another alternative embodiment is shown in FIG. 6 where the alpha angle and the beta angle are greater than 90°. In another alternative embodiment as shown in FIGS. 10 and 11, the alpha angle is about 0° and the beta angle is about 0°. Accordingly the tube blank perimeter is substantially the same as the grip region 17 perimeter as defined by the ridges 32.

Referring primarily to FIG. 2, each corrugation has a trough 31, ridge 32, length 29, and a width 30. Referring to FIG. 3, each corrugation 23 is comprised of a trough 31 and a ridge 32. Referring to FIG. 2, the corrugations 23 are formed by folding the material into a series of alternating ridges 31 and troughs 32 (as shown in FIG. 3) where the transition radius at the fold between two adjoining trough or ridge walls can be tight analogous to the bottom of the capital letter "V" in Arial typefont or more gentle or curved analogous to the bottom of the capital letter "U" in Axial type-font. Further, the corrugations can be tilted such that the cross-section appears like italicized capital letters "U" and "V" in Axial type-font.

The corrugations 23 may be formed to have essentially identical lengths and widths. Alternatively, the corrugations 23 may be of differing lengths and widths. For example, the lengths and/or widths of the corrugations may be selected to alternate between a first length dimension and a second length dimension which are different from one another. The differing lengths 29 and/or widths 30 of the corrugation 23 may be random or arranged in a pattern. The number of differing length 29 and width 30 dimensions may be two or more.

The manufacturer of the tampon applicator may vary the size of each corrugation, the number of the corrugations, and the distance over which the corrugations 23 extend.

The size of each of the corrugation 23 can vary greatly. The size of each corrugation 23 is a function of the number of corrugations times two times the depth 19 of the corrugation 23.

Any number of corrugations 23 may be utilized. The number of the corrugations 23 may range from 1 to 50 corrugations. Either an even or an odd number of corrugations 23 can be present and the corrugations 23 can be equally spaced apart or they can be non-uniformly arranged. Uniformly arranged corrugations 23 are preferred but randomly arranged corrugations 23 will work. For ease of manufacturing, it is preferred that the corrugations 23 be equally spaced relative to one another. The corrugations, however, may be unequally spaced relative to one another.

The distance between each corrugation 23 which extends along the perimeter of the grip region 17 depends on the perimeter of the insertion member 11 and the size of each corrugation 23.

When a user inserts the tubular insertion member 11 into a body cavity, her fingers and/or thumb are urged towards the insertion end 13 due to frictional forces between the insertion member 11 and the walls of the body cavity. The second transition portion 21 and the plurality of corrugations 23 provides resistance to this movement, thereby providing a secure hold. Once the tubular insertion member 11 is successfully inserted into the body, a user can then expel material contained by the applicator. This is typically performed by displacing an elongate expulsion member, shown as element 22, into the tubular insertion member 11. During the expulsion step, her fingers and/or thumb are urged towards the gripper end 14 due to the potential combination of many factors, such as the frictional forces between insertable material and the inner wall of the tubular insertion member 11, and the forces required to open the insertion end 13. The first transition portion 20 provides resistance to this movement. The grip region 17 itself provides improved handling of the applicator because the corrugations 23 increases the grip.

Tampon Applicator Materials

The tampon applicator 10 includes an insertion member 11 and an elongate expulsion member 22. The insertion member 11 is preferably in the form of a spirally wound, convolutely wound or longitudinally seamed hollow tube which is formed from paper, paperboard, cardboard or a combination thereof. The insertion member 11 may also be injection molded or formed from flexible plastic, such as thermoformed from plastic sheet or folded or wound from plastic film. The insertion member 11 may also be formed from a combination of paper and plastic. The insertion member 11, also commonly referred to as an outer tube, is fairly rigid and has a relatively small diameter of about 10 millimeters to about 20 millimeters. The insertion member 11 has a wall with a predetermined thickness of about 0.1 millimeters to about 0.7 millimeter.

The wall can be constructed from a single ply of material or be formed from two or more plies that are bonded together to form a laminate.

The use of two or more plies or layers is preferred for it enables the manufacturer to use certain materials in the various layers that can enhance the performance of the tampon applicator 10. When two or more plies are utilized, all the plies can be spirally wound, convolutely wound or longitudinally seamed to form an elongated cylinder. The wall can be constructed using a smooth thin ply of material on the outside or exterior surface that surrounds a coarser and possibly thicker ply. When the wall contains at least three plies, the middle ply can be the thicker ply and the interior and exterior plies can be smooth and/or slippery to facilitate expulsion of the tampon and to facilitate insertion of the insertion member 11 into a woman's vagina, respectively. By sandwiching a thick, coarser ply of material between two thin, smooth plies, an inexpensive insertion member 11 can be provided which is very functional. The wall should contain one to four plies, although more plies can be utilized if desired.

The plies forming the wall can be held together by an adhesive, such as glue, or by heat, pressure, ultrasonics, etc. The adhesive can be either water-soluble or water-insoluble. A water-soluble adhesive is preferred for environmental reasons in that the wall will quickly break apart when it is immersed in water. Such immersion will occur should the insertion member 11 be disposed of by flushing it down a toilet. Exposure of the insertion member 11 to a municipal's waste treatment plant wherein soaking in water, interaction with chemicals and agitation all occur, will cause the wall to break apart and evenly disperse in a relatively short period of time.

The inside diameter of the insertion member 11 is usually less than about 0.75 inches (about 19 mm) and preferably less than about 0.625 inches (about 16 mm). Although the exterior diameter of tampons do vary, most tampons utilized by women have an external diameter of less than about 0.75 inches (about 19 mm). However, if one desired to use this invention to administer medication to an animal, such as a farm animal or other mammal, larger size tampons which would require insertion members with a larger diameter could be used.

Alternatively, the material can be overlapped into a tubular configuration. Spirally or convolutely winding the insertion member 11 into a cylindrical tube is especially advantageous when the insertion member 11 is formed from a laminate. The reason for this is that when a laminate is circumferentially wound into a tube and a butt seam or an overlap is formed, the butt seam or the overlap can interfere with the later formation of corrugations 23. A common problem with a rigid or stiff walled, tubular member having a relatively small diameter and a butt seam is that the seam has a tendency to come apart after formation if exposed to certain stress forces and/or high humidity. A problem with a tubular member having an overlap is that a small portion of the wall will be thicker than the remaining portion and this will cause problems when one tries to corrugate one end of the tube. Accordingly, the insertion member 11 should preferably be formed into a cylindrical configuration without the presence of a butt seam or an overlap. In the case of other tube construction methods such as fiber or plastic molding, or integral tube forming (e.g. thermoforming plastic) no seams will be present and the corrugations could optionally be formed as part of the tube molding or forming process.

The insertion member 11 is sized and configured to house an absorbent tampon. As stated above, the insertion member 11 should have a substantially smooth exterior surface that will facilitate insertion of the insertion member 11 into a woman's vagina. When the exterior surface is smooth and/or slippery, the insertion member 11 will easily slide into a woman's vagina without subjecting the internal tissues of the vagina to abrasion. The insertion member 11 can be coated to give it a high slip characteristic. Wax, polyethylene, a combination of wax and polyethylene, cellophane and clay are representative coatings that can be applied to the insertion member 11 to facilitate comfortable insertion.

Optional Features

Optional materials may be added to the finger gripping region for a variety of reasons. These materials may be added as an indicator for where a user should grasp the applicator, as an indicator for differentiating products such as different absorbency tampons, and the like. Additionally, materials may be added within the grip region 17 to further increase resistance to finger slip through increased friction or to maintain the grip region 17 once it is formed, thereby minimizing the tendency for the grip region 17 to "spring back." Preferred materials are elastomers such as rubber; other polymeric materials, such as those that are shrinkable upon exposure to sufficient energy; and pigments or dyes.

The insertion member 11 can be a straight, elongated cylindrical tube formed on a central longitudinal axis X-X. It is also possible to form the insertion member 11 into an arcuate shape. The arcuate or curved shape can assist in providing comfort when inserting the insertion member 11 into a woman's vagina. With a curved tampon applicator, it is possible to employ a curved tampon which again may be more comfortable for some women to use since the shape of the tampon may better fit the curvature of a woman's vagina.

The applicator of the present invention can be used for the delivery of catemenial devices, such as tampon, intravaginal collection device, and interlabial pads. The applicator may also be useful for oral, rectal, and vaginal suppositories, as well as nasal devices, such a nasal tampons. Further the applicator can be used for delivery of various other materials including, medicaments, moisturizers, vitamins and minerals, spermicides, and odor controlling agents. These materials may be in the form of solids, creams, foams, gels, and the like.

III. Method of Making the Tampon Applicator of the Present Invention

A method of manufacturing a tampon applicator having a corrugated region of the present invention involves the following steps: providing a tampon applicator having a first end, a second end, a length and a diameter and forming a plurality of corrugations in said tampon applicator, said corrugations defining said corrugated region, each of said corrugations having a ridge and a trough.

Details of the above described method as well as other methods which may be used to form the tampon applicators of the present invention are found in co-pending case Ser. No. 10/179,087, filed Jun. 25, 2002 entitled "METHOD OF PRODUCING A CORRUGATED TAMPON APPLICATOR", to "Fedyk et. al.".

The disclosures of all patents and patent applications referred to in this specification (including those listed in the Cross Reference to Related Applications Section) are hereby incorporated by reference as if fully set forth herein. While particular embodiments of the present invention have been illustrated and described, it would be obvious to those skilled in the art that various other changes and modifications can be made without departing from the spirit and scope of the invention.

What is claimed is:

1. A tampon applicator comprising:
    an elongate insertion member having a length extending from an insertion end to a gripper end opposite thereof, the gripper end comprising a grip region dimensioned to substantially accept a user's grip;
    said grip region having a depth and comprising a plurality of corrugations, a first transition portion, and a second transition portion, wherein said first transition portion provides resistance to the movement of at least a user's finger or thumb towards the gripper end, and said second transition portion provides resistance to the movement of at least a user's finger or thumb towards the insertion end;
    each of said plurality of corrugations comprising a trough and a ridge wherein said trough is concave and said ridge is convex, wherein said trough and ridge are aligned along their length with said length of said elongate insertion member in said grip region;
    said first transition portion being substantially adjacent said gripper end and said second transition portion being substantially adjacent to said insertion end; and
    wherein said first transition portion and said grip region span a radial arc identified as angle alpha ($\alpha$) and said second transition portion and said grip region span a radial arc identified as angle beta ($\beta$).

2. The tampon applicator of claim 1 wherein said angle alpha ($\alpha$) is greater than 90°.

3. The tampon applicator of claim 1 wherein said angle alpha ($\alpha$) is less than 90°.

4. The tampon applicator of claim 1 wherein said angle beta ($\beta$) is greater than 90°.

5. The tampon applicator of claim 1 wherein said angle beta ($\beta$) is less than 90°.

6. The tampon applicator of claim 1, further comprising an elongate expulsion member.

7. In combination, a tampon applicator and a tampon, said combination comprising:
    a) tampon;
    b) an elongate insertion member having a length extending from an insertion end to a gripper end opposite thereof, the gripper end comprising a grip region dimensioned to substantially accept a user's grip;
    c) said grip region having a depth and comprising a plurality of corrugations, a first transition portion, and a second transition portion, wherein said first transition portion provides resistance to the movement of at least a user's finger or thumb towards the gripper end, and said second transition portion provides resistance to the movement of at least a user's finger or thumb towards the insertion end;
    d) each of said plurality of corrugations comprising a trough and a ridge wherein said trough is concave and said ridge is convex, wherein said trough and ridge are aligned along their length with said length of said elongate insertion member in said grip region;
    e) said first transition portion being substantially adjacent said gripper end and said second transition portion substantially adjacent to said insertion end; and
    f) wherein said first transition portion and said grip region span a radial arc identified as angle alpha ($\alpha$) and said second transition portion and said grip region span a radial arc identified as angle beta ($\beta$).

8. The tampon applicator of claim 7, further comprising an elongate expulsion member slideably mounted in said gripper end of said elongate insertion member.

* * * * *